(12) United States Patent
Matsuura

(10) Patent No.: US 6,212,432 B1
(45) Date of Patent: Apr. 3, 2001

(54) METHOD, APPARATUS AND SYSTEM USING A PLURALITY OF LOW-FREQUENCIES FOR THERAPY

(76) Inventor: Masayuki Matsuura, 477-11, Higashimikata-cho, Hamamatsu-shi, Shizuoka-ken 433-8104 (JP)

( * ) Notice: Subject to any disclaimer, the term of this patent is extended or adjusted under 35 U.S.C. 154(b) by 0 days.

(21) Appl. No.: 09/194,430
(22) PCT Filed: May 30, 1997
(86) PCT No.: PCT/JP97/01849
 § 371 Date: Nov. 30, 1998
 § 102(e) Date: Nov. 30, 1998
(87) PCT Pub. No.: WO97/45159
 PCT Pub. Date: Dec. 4, 1997

(30) Foreign Application Priority Data

May 31, 1996 (JP) .................................................. 8-137950

(51) Int. Cl.<sup>7</sup> ..................................................... A61N 1/32
(52) U.S. Cl. ................................. 607/76; 607/50; 607/63
(58) Field of Search ............................... 607/50, 59, 63, 607/76

(56) References Cited

U.S. PATENT DOCUMENTS 5,658,322 * 8/1997 Fleming .................................. 607/50

FOREIGN PATENT DOCUMENTS

| 354578 | * | 2/1990 | (EP) | ....................................... 607/63 |
| 1011128 | * | 4/1983 | (SU) | ....................................... 607/50 |
| 1159582 | * | 6/1985 | (SU) | ....................................... 607/50 |

* cited by examiner

Primary Examiner—Carl H. Layno
(74) Attorney, Agent, or Firm—Arent Fox Kintner Plotkin & Kahn, PLLC

(57) ABSTRACT

An oscillating unit (12) of a low-frequency therapeutic apparatus (10) is controlled by a frequency control device (18) to generate plural frequencies chosen from the frequencies determined in advance according to the disease of interest, and these frequencies are delivered from the lowest in an ascending order at specified time intervals.

26 Claims, 6 Drawing Sheets

FIG.2

| DISEASE NAME NO. | FREQUENCY (Hz) |
|---|---|
| 001 | 20, 60, 72, 95, 125, 666, 727, 740, 787, 790, 880, 5000, 10000 |
| 002 | 666, 727, 740, 787, 790, 880, 5000 |
| 003 | 666, 727, 740, 787, 790, 880, 10000 |
| 004 | 20, 60, 72, 95, 125, 5000 |
| 005 ⋮ | ⋮ |

METHOD, APPARATUS AND SYSTEM USING A PLURALITY OF LOW-FREQUENCIES FOR THERAPY

TECHNICAL FIELD

This invention relates to a method, apparatus and system for low-frequency therapy.

BACKGROUND ART

Conventionally, electric therapeutic machines have been used as a sort of physical therapy, and a part of the electric therapeutic machine includes a low-frequency therapeutic apparatus which aims at treating a disease by applying electrodes on the surface of skin of a patient, and passing therewith a low-frequency current through the patient's body.

The low-frequency therapeutic apparatus comprises a therapeutic electrode (active electrode) applied on a site to be treated, and an inactive electrode to couple with the above electrode, and applying a low-frequency electric current between the two electrodes via a voltage delivered from an oscillator.

Such a low-frequency therapeutic apparatus is required, for example by Japanese Industrial Standards, to have an oscillator which can generate waves of at least one frequency for each of four bands of not more than 5 Hz, 5–50 Hz, 50–500 Hz and 500–1000 Hz.

Such a low frequency therapeutic apparatus has been used for the purpose of, for example, prevention of disuse atrophy of paralyzed muscles, pain relief and recovery of failed local blood circulation, through stimulation by way of electric currents. Furthermore, particularly a small low-frequency therapeutic apparatus has been used for relaxing stiffened shoulder muscles.

The conventional low-frequency therapeutic apparatuses as described above have been exclusively used for stimulation of muscles, pain relief, and recovery of failed circulation, but remains practically ineffective for the treatment of definitive diseases.

DISCLOSURE OF THE INVENTION

This invention aims at providing a method, apparatus and system for low-frequency therapy capable of effectively treating definitive diseases by applying a low-frequency current.

One aspect of this invention relating to the method achieves above object by providing a low-frequency therapy comprising passing a current of a low-frequency through the patient's body from the skin wherein at least a part of 1–10000 Hz is chosen as the frequency of low-frequency current, and a series of those frequencies are delivered step by step in an ascending order at specified time intervals.

This method is based on the findings the present inventors have obtained themselves through experimentation. Namely, the inventors have found that, when an electric current is passed through a human body, the effective lowest frequency varies according to the kind of disease, but more or less damaged cells pass more readily the current than do normal cells. To put it otherwise, an electric current of a low frequency tends to pass more readily through damaged sections within a human body. Hence, when the current passing through the patient's body is gradually increased in its frequency, the most seriously damaged parts receive the current most amply at first, which are followed step by step by less damaged parts, and thus treatment proceeds from more damaged parts to less damaged parts in order.

As for the therapeutic effect, the following assumption may be offered: if for example a cell has its membrane so sclerosed as to disrupt the interchange of intracellular and extracellular fluids, or if for example a nerve cell can not or can scarcely transmit nerve impulses as a result of sclerosis, stimulation of the cell or nerve cell by passing a weak current whose frequency is raised step by step at specified intervals will soothe the stiffness these cells have undergone, to recover their normal activity which will eventually result in the subsidence of disease or healing of the disease.

The present inventors have made another discovery that an electric current having a specific frequency (for example chosen from 69 specific kinds of frequencies between 1 and 10000 Hz) has a particularly notable therapeutic effect.

This invention comprises selecting in advance plural kinds of frequencies, and applying a low-frequency current having the thus selected frequencies for therapy.

This is because, as different cells, muscle systems, blood vessels and lymphatics, and nervous systems are involved according to the kind of disease, it is necessary for achieving a quite satisfactory therapeutic effect to choose appropriate frequencies according to the type of cells involved in the disease of interest, and to combine those frequencies for therapy.

According to this invention, the appropriate frequency to be chosen includes 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz and the therapy consists of selecting a part thereof.

This invention is characterized by including a basic therapy consisting of applying an electric current having frequencies of 20, 60, 70, 72, 75, 125, 666, 727, 740, 787, 790 and 10000 Hz in this order, and, an adaptive therapy consisting of applying another current having frequencies previously chosen as appropriate according to the kind of disease to be treated.

This invention is characterized by applying plural times in repetition a low-frequency current having a part of the choice frequencies as described above to the patient's body for therapy.

Further, this invention is characterized by applying in repetition a low-frequency current having the highest choice frequency as described above to the patient's body for therapy.

This invention adopts 20 Hz as the lowest of all the choice frequencies as described above.

Alternatively, this invention adopts 666 Hz as the lowest of all the choice frequencies as described above.

Furthermore, this invention adopts 10000 Hz as the highest of all the choice frequencies as described above.

Still further, this invention adopts 5000 Hz as the highest of all the choice frequencies as described above.

One aspect of this invention relating to the therapeutic apparatus achieves above object by providing a low-frequency therapeutic apparatus comprising a therapeutic electrode to be applied to a treated site, an inactive electrode placed on the same human body in conjunction with the therapeutic electrode for passage of electric current through the body, and an oscillating unit generating a weak electric current having a low-frequency to be given between the two electrodes, wherein the oscillating unit contains a frequency control device which chooses from among plural frequencies previously selected from at least part of 1–10000 Hz, and achieves a switching of the thus chosen frequencies in an ascending order at specified time intervals.

Another aspect of this invention relating to the therapeutic apparatus provides the low-frequency therapeutic apparatus which further comprises a memory section to memorize the data of plural frequencies previously chosen appropriately in accordance with the kind of disease, and a selection signal delivering section to read from the memory section the data of plural frequencies previously chosen as described above, in response to an instruction signal fed in accordance with the kind of disease to be treated, and to achieve a switching of oscillation frequencies of wave from the oscillating unit according to the thus read data in an orderly fashion.

According to still another aspect of this invention relating to the therapeutic apparatus, the plural frequencies chosen in advance include a part of 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

According to still another aspect of this invention, the frequencies chosen for the basic therapy introduced before the therapy specific for the disease of interest include 20, 60, 70, 72, 75, 125, 666, 727, 740, 787, 790 and 10000 Hz.

One aspect of this invention relating to the therapeutic system achieves above object by providing a low-frequency therapeutic system comprising a therapeutic electrode to be applied to a treated site, an inactive electrode placed on the same human body to couple with the therapeutic electrode for passage of electric current through the body, an oscillating unit generating a weak electric current having a frequency of 1 to 10000 Hz to be given between the two electrodes, a frequency selecting device to switch, in response to an incoming frequency selection signal, the current oscillation frequency of wave from the oscillating unit to the designated frequency, and a frequency selection control device to choose oscillation frequencies from among the previously chosen plural frequencies in the range of at least a part of 1 to 10000 Hz, to arrange them in an ascending order for delivery at specified time intervals, and to deliver them as respective frequency selection signals to the frequency selecting device.

As described above, the oscillating unit and the frequency selection control device which delivers information regarding the frequency of wave to be generated by the oscillating unit are separated from each other, and thus it is possible for the frequency selection control device at one site to control multiple oscillating units at different places by linking itself with them through telecommunication lines, and thus to lower the overall cost. Besides this it is also possible, even when a new disease is recently added through research to the list of treatable diseases, the therapeutic frequencies effective for that disease can be readily utilized by all the member oscillating units without the need for updating the current contents of memory of those individual oscillating units.

Another aspect of this invention relating to the system further provides a system wherein the frequency selection control device comprises a memory section to store the data of plural frequencies to be chosen in accordance with the kinds of diseases, and a signal delivering section to read, in response to an instruction signal fed in accordance with the kind of disease of interest, the aforementioned data giving the appropriate plural frequencies to be chosen in accordance with that kind of disease, and to deliver them as frequency selection signals step by step in an ascending order to the frequency selection device.

Still another aspect of this invention relating to the system provides the frequency selection control device which delivers the selection signal to the frequency selecting device through wired or wireless telecommunication lines.

According to still another aspect of this invention relating to the system, the plural frequencies include a part of 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

According to still another aspect of this invention relating to the system, the frequencies chosen for the basic therapy introduced before the therapy specific for the disease of interest include 20, 60, 70, 72, 75, 125, 666, 727, 740, 787, 790 and 10000 Hz.

BRIEF DESCRIPTION OF THE DRAWINGS

FIG. 2 is a table giving the content of memory stored in the memory section of the same low frequency therapeutic apparatus.

BEST MODE FOR CARRYING OUT THE INVENTION

Embodiments of this invention will be described in detail below with reference to the drawings.

Figure 1:
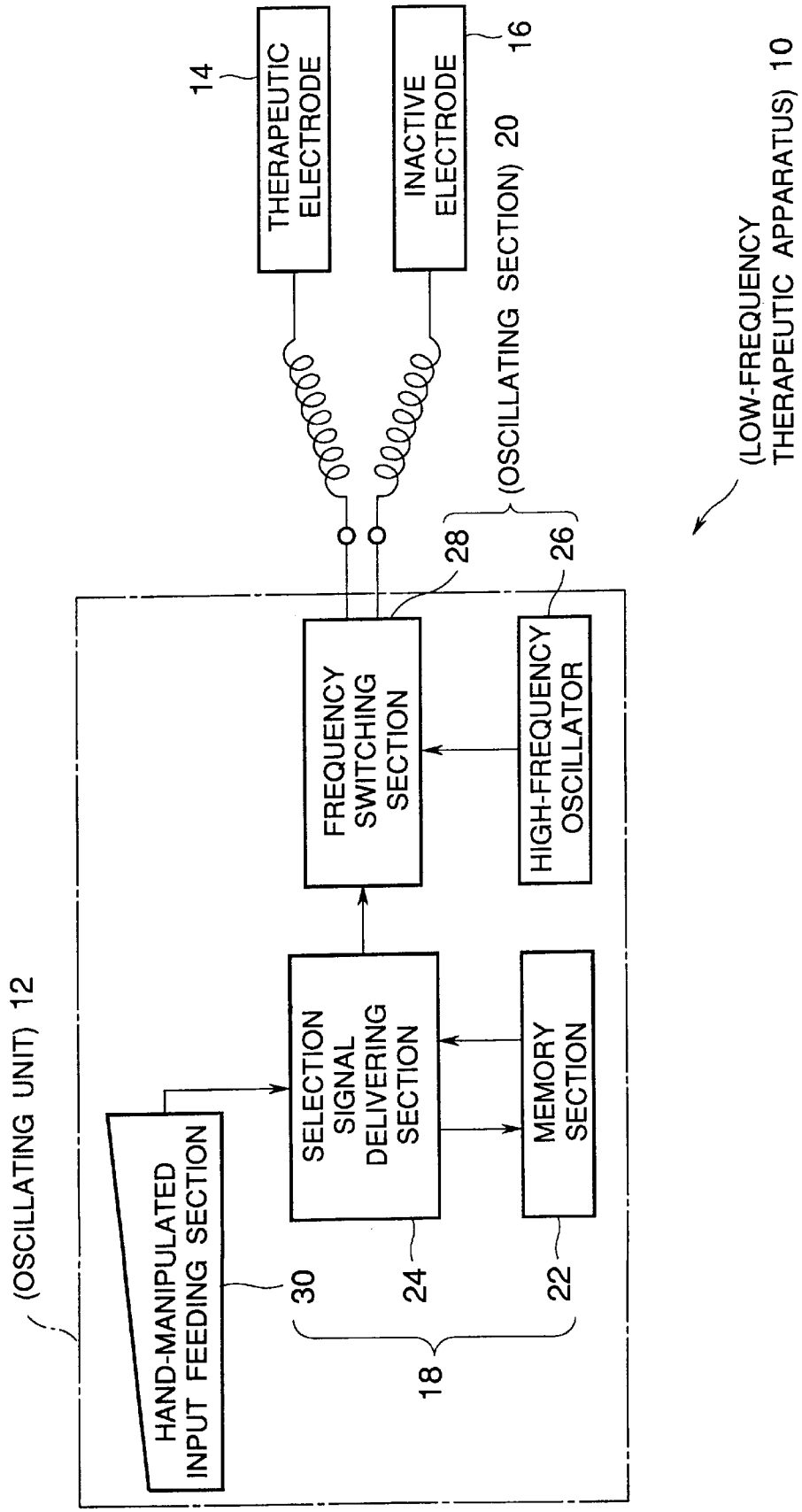
FIG. 1 is a block diagram illustrating a low-frequency therapeutic apparatus embodying this invention.

As shown in FIG. 1, a low-frequency therapeutic apparatus 10 of this invention comprises an oscillating unit 12 generating a weak current of a low frequency, and a therapeutic electrode 14 and an inactive electrode 16 which receive the current generated by the oscillating unit 12.

The therapeutic electrode 14 is an electrode to be applied to a site on human body which requires treatment, while the inactive electrode 16 or the paired electrode to the therapeutic electrode 14, is an electrode to be applied on the same body for passage of electric current through the body.

The therapeutic and inactive electrodes 14 and 16 are composed, for example, of a conductive rubber plate or of a conductive adhesive sheet attached on the surface of a conductive rubber plate, and they can be closely attached to the surface of human body.

The oscillating unit 12 comprises a frequency control device 18 to choose oscillation frequencies from among plural frequencies previously selected from the range of 1–10000 Hz, and to arrange them step by step in an ascending order at specified time intervals for delivery, and an oscillating section 20 to oscillate the current according to control signals delivered by the frequency control device 18.

The present inventors have found through experimentation that an electric current having following 69 frequencies in the range of 1–10000 Hz has a particularly notable therapeutic effect. Electric currents having other frequencies were either barely effective or ineffective or even harmful. The plural frequencies described above are chosen from following 69 frequencies, i.e., 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

The frequency control device 18 further comprises a memory section 22 to memorize plural frequency data previously chosen appropriately in accordance with the kinds of diseases, a selection signal delivering section 24 to read, from the memory section 22, appropriate frequencies from among plural frequencies previously chosen as described above, in response to an instruction signal fed in accordance with the kind of disease to be treated, and to change the oscillation frequency of wave from the oscillating section 20 according to the currently read frequency data in an orderly fashion, and a hand-manipulated input feeding section 30 to be described below.

The oscillating section 20 comprises a high frequency oscillator 26, and a frequency modifying section 28 which contains a revolving device to revolve round the frequencies generated by the high frequency oscillator 26, and converts a high frequency of electric current generated by the high frequency oscillator 26 into a frequency corresponding with one of the plural frequencies previously chosen, in accordance with an instruction signal delivered by the selection signal delivering section 24.

The memory section 22 stores numbers representing the kinds of diseases and data of frequencies appropriate for the kind of diseases in the form of table as presented in FIG. 2. Take arteriosclerosis as an example. A No. 001 representing that disease and appropriate frequencies to be selected comprising 20, 60, 70, 95, 125, 666, 727, 740, 787, 790, 880, 5000 and 10000 Hz have been stored in memory ready for use. Take allergy as another example. A No. 002 representing the disease and appropriate frequencies to be selected comprising 7 frequencies in total of 666, 727, 740, 787, 790, 880 and 10000 Hz have been stored in memory.

The selection signal delivering section 24, when the operator feeds an instruction signal through the hand-manipulated input feeding section 30 according to the kind of disease of interest, for example, No. 001 for arteriosclerosis, No. 002 for allergy, No. 003 for anorexia, etc., reads, from the memory section 22, plural frequency data appropriate for the kind of disease, and delivers them as output.

Incidentally, with this low-frequency therapeutic apparatus, electricity applied to the therapeutic and inactive electrodes 14 and 16 has a maximum voltage of 30V and a maximum current of 50 mA, and they are below the voltage and current limits over which damages of the human body (or of cells) will result.

The duration of current application is determined for example as three minutes for each frequency, and principally no interruption is necessary at each switching from one frequency to another, but such an interruption may be inserted as appropriate. Further, the duration of three minutes may be somewhat lengthened or contracted.

For treatment, for example, of arteriosclerosis, the therapeutic electrode 14 and the inactive electrode 16 are applied on the skin adjacent to the one and another ends of the artery suffering from sclerosis, and an electric current is passed between the two electrodes. For the treatment of anorexia, the therapeutic and inactive electrodes 14 and 16 are applied one on the frontal skin and the other on the dorsal skin covering the stomach or intestine, so that the two electrodes sandwich the affected organ and a current is allowed to pass through that organ.

Figure 3:
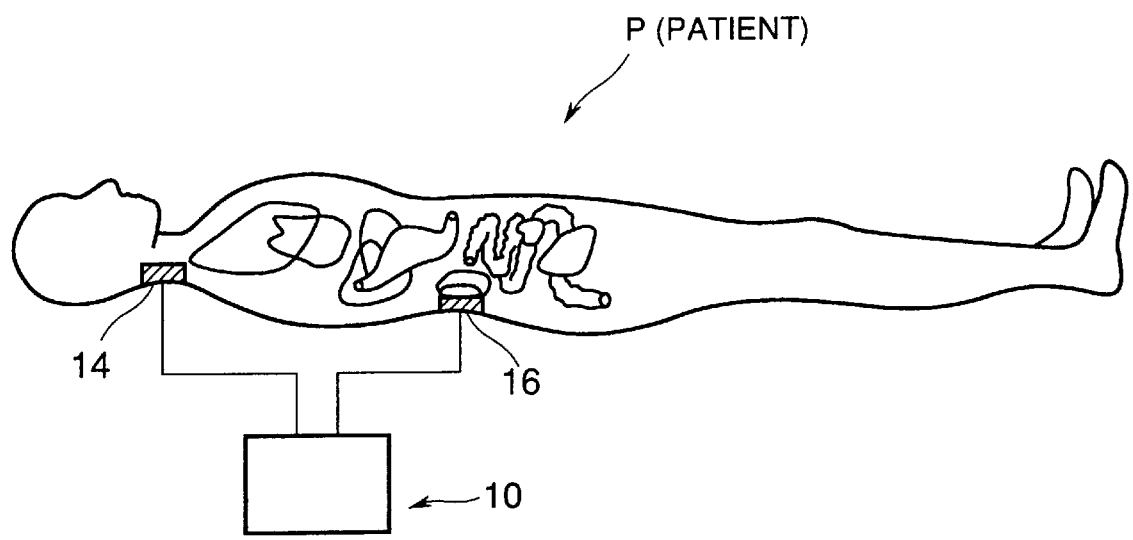
FIG. 3 is a lateral view to illustrate how treatment proceeds with the same low-frequency therapeutic apparatus.

Some kinds of diseases are often caused by a distorted spinal column, or abnormal disposition or imbalance of muscles placed on both sides of the spinal column. For treatment of such a disorder, as shown in FIG. 3, the electrodes 14 and 16 are applied one on the posterior surface of neck of the patient P and the other on the posterior surface of upper sacrum, and an electric current is passed between the two electrodes.

Figure 4:
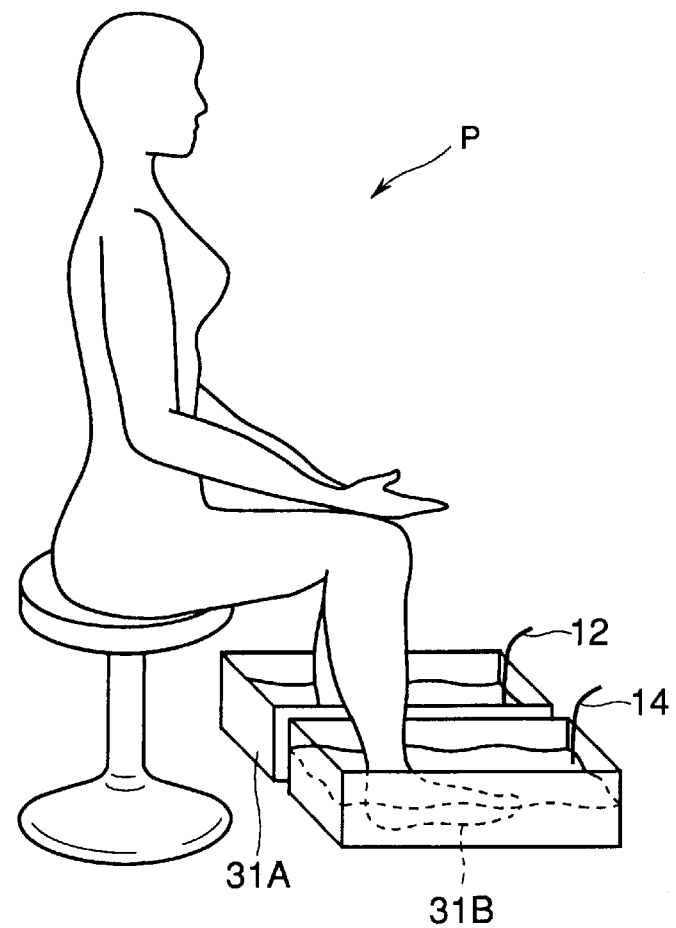
FIG. 4 is a lateral view to illustrate how treatment proceeds with the same low-frequency therapeutic apparatus.

As still another application, for treatment of a lesion located anywhere from the toe to the part just beneath the navel, as shown in FIG. 4, therapy consists of pouring warm water into two basins 31A and 31B, dissolving a small amount of electrolytes such as table salt in the two volumes of water to reduce the electric resistance thereof, having the patient P put his/her feet (from the toe to the heel) one for each basin, placing the therapeutic and inactive electrodes 14 and 16 separately for each basin, and passing an electric current between the two electrodes. For the treatment of a patient having a systemic or chronic disease, therapy consists of having the patient put his/her feet together in one basin, inserting one electrode into the same basin and placing the other electrode on the neck, and passing a large amount of electrons through the body.

Figure 5:
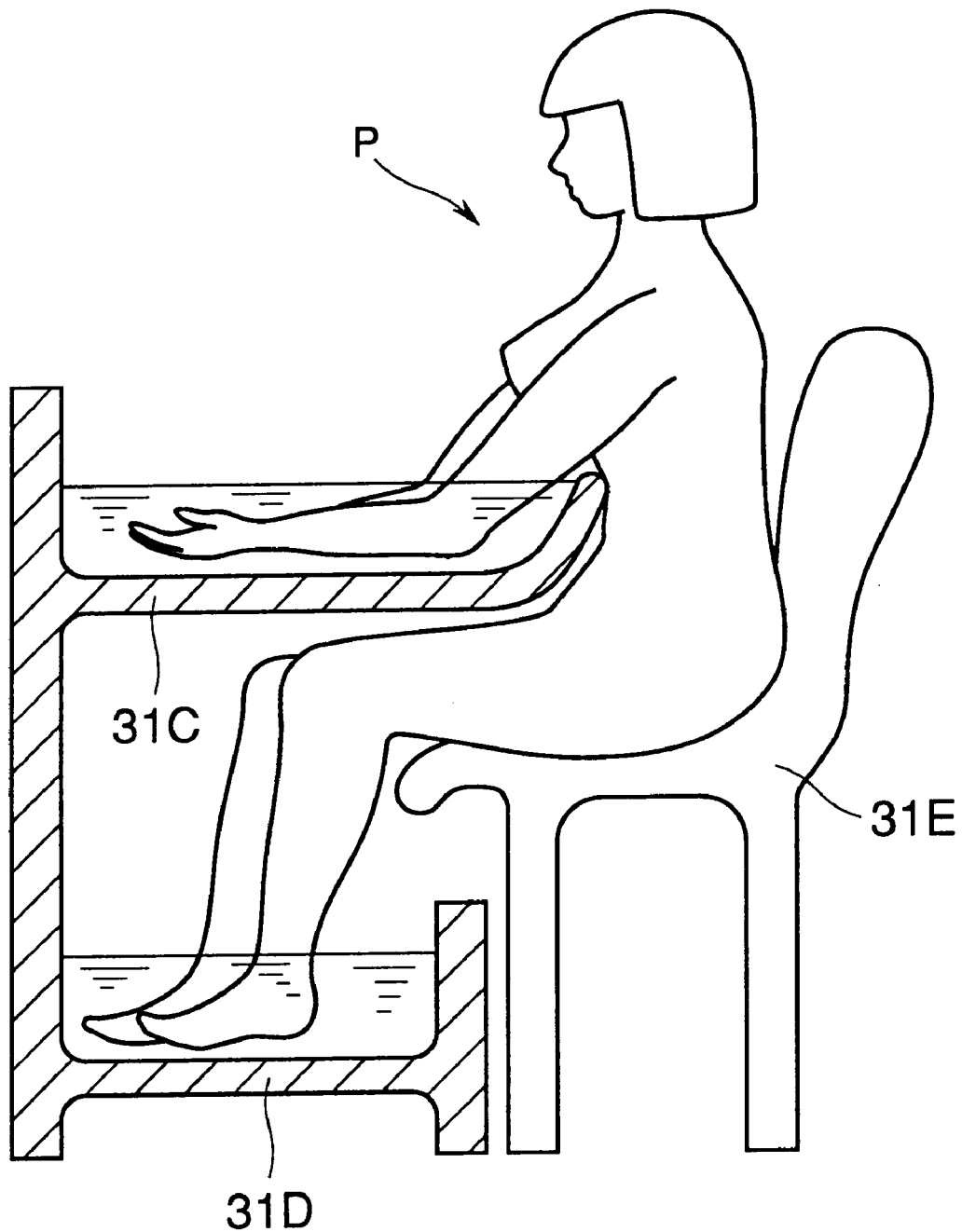
FIG. 5 is a diagrammatic lateral view to illustrate another example of treatment with the same apparatus.

An alternative therapy may consist of having the patient putting his/her both hands and feet in two basins 31C and 31D separately as shown in FIG. 5, pouring warm water dissolving table salt into the two volumes of water, placing the therapeutic and inactive electrodes 14 and 16 separately in the two basins 31C and 31D, and passing an electric current between the two electrodes. In this case, the patient is allowed to sit on a chair 31E during therapy.

The present inventors found that, prior to the therapy specific for a disease of interest, introduction of a basic therapy which contributes to shift the pH of bodily fluid of the patient which has been displaced towards acidity, to weak alkalinity will bring about a great therapeutic effect.

Figure 6:
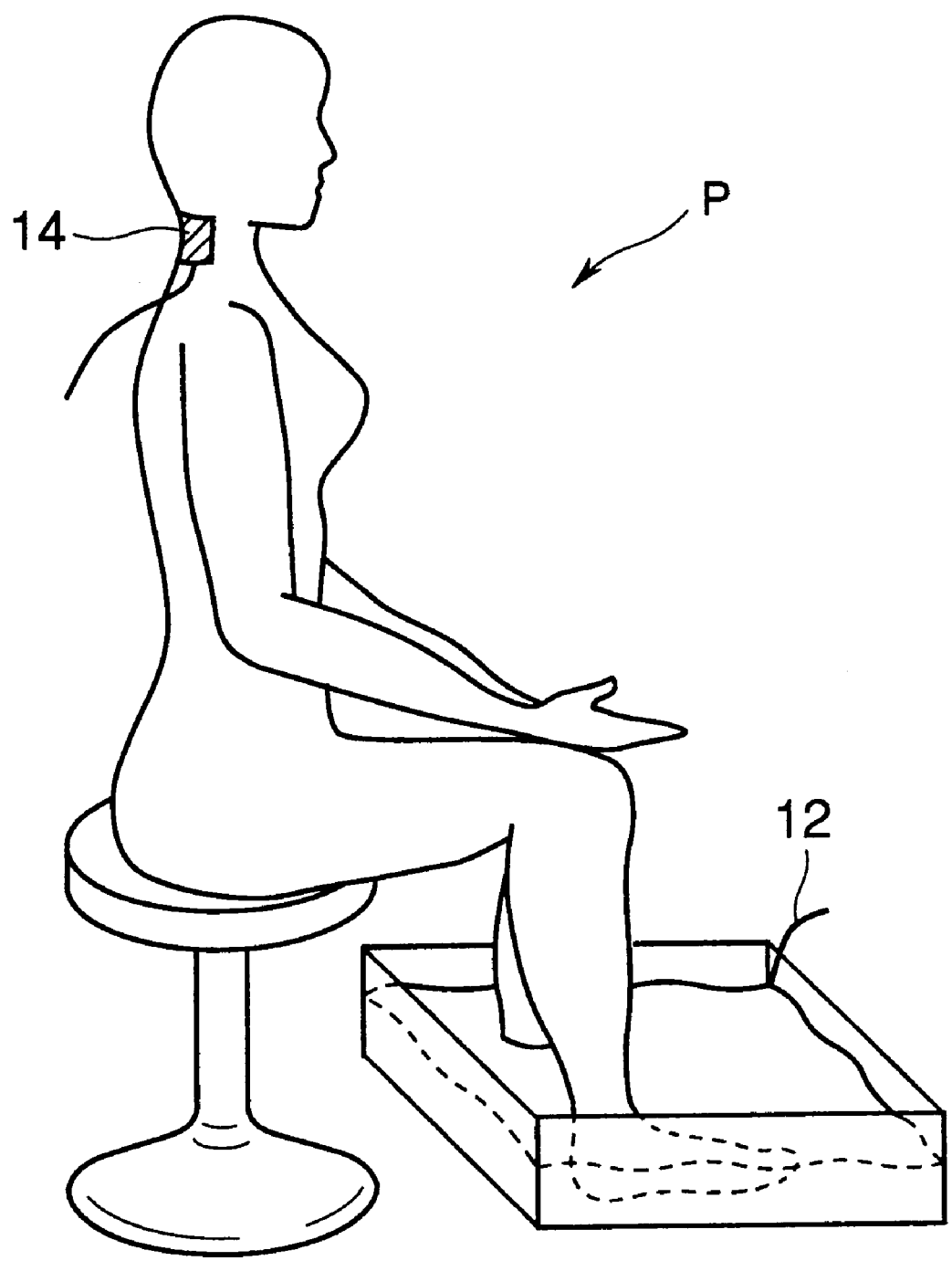
FIG. 6 is a perspective view to illustrate the basic therapy.

The basic therapy, as shown in FIG. 6, consists of placing one of the therapeutic and inactive electrodes 14 and 16 into a basin 31, having the patient P put his/her bilateral feet into the same basin 31, applying the other electrode on the posterior part of patient's neck, and passing an electric current between the two electrodes. The basin 31 is filled with warm water dissolving table salt or the like.

The frequency of electric current includes 20, 60, 70, 72, 125, 666, 727, 740, 787, 790 and 10000 Hz, and these frequencies are applied across the two electrodes in this order.

On completion of this basic therapy, therapy (adaptive therapy) consisting of passage of an electric current having frequencies appropriate for the disease sustained by the patient P is undertaken.

In this case, the used frequencies may be totally or partly the same with those of basic therapy or may be totally different from the latter. In addition, the sites of the patient P for application of electrodes 14 and 16 for the adaptive therapy may be the same with or different from those for the basic therapy.

According to clinical experience, for example in the treatment of hypoacusis, therapy consists of passing an electric current between the two ears, and the patient receiving the therapy came to perceive high frequency sounds considerably well which have been practically inaccessible to perception heretofore. Further, when an electric current was passed between the bilateral temples, the patient came to have an improved vision.

In addition to arteriosclerosis, allergy and anorexia described above, the therapy was also effective for the treatment of 327 different diseases including, to mention a few, asthma, anemia, arthritis, appendicitis/inflamed cecum/ pneumonia, hypotension, burn, nephritis, hypertension, constipation, cystitis, cancer, etc.

However, the definitive reason why the therapy consisting of raising the frequencies of electric current step by step in an ascending order is effective for the treatment of those diseases as described above can not be offered yet.

Only the following assumption may be presented.

Firstly, each cell has on its cell membrane many ionic channels, but, when it has its cell membrane sclerosed, these ionic channels become closed making it impossible to interchange ions such as calcium ions, sodium ions, potassium ions, etc. between the intracellular and extracellular spaces, or reducing such interchange to an extremely marginal level. In this state, the patient may be often afflicted with a so-called ionic-channel failure disease. Sclerosis of cell membrane may result from the injurious effect due for example to oxygen radicals.

As another possible cause, a biochemical phenomenon or a so-called calcium paradox may be mentioned. When the calcium concentration in blood lowers for some reason, calcium constituting bones dissolves into blood, and the dissolved calcium in blood is pushed into the interior of cells through the action of hormones, and the involved cells are exposed to a so-called calcium toxin and become sclerotic. Although calcium is one of minerals essential for the vital activity, calcium excessively dissolved in blood is rather harmful to a living body.

As a third possible cause, the following may be mentioned. With respect to muscle cells, calcium enters into the cell interior to act as a trigger for contraction, but, when muscle cells generate lactic acid after a hard exercise, calcium binds to lactic acid thus generated to form calcium lactate which may cause the involved muscle cells to harden.

As a further postulate, the inner wall of an artery is constituted by smooth muscle cells, and, when calcium binds to those smooth muscle cells, the involved cells become so sclerotic that they can not maintain the elasticity of the artery. To compensate for this defect, a new growth of smooth muscle cells occurs over the hardened cells, and such processes are repeated one after another to gradually narrow the cross-sectional area of the artery. This is a known cause for the development of so-called arteriosclerosis.

Even such sclerotic cells, when being exposed to an electric current, naturally contract. When the stimulating current occurs as an alternating current, the involved cells may repeat contraction and relaxation. During the stimulation, however, sclerotic cells do not respond uniformly to all frequencies of stimulating current but contract in response to certain specific frequencies.

Generally, more seriously hardened cells become more responsive to lower frequencies, because they have lost more severely their elasticity. For example, when a hardened cell is exposed to a current having a frequency of 15 Hz, it vibrates just as it is put in resonance with the stimulation, and through the vibration, the sclerotic membrane of the cell is relaxed and resumes a certain degree of elasticity. Accordingly, the cell which has resumed a certain degree of elasticity after being stimulated for example with a current of 15 Hz frequency, becomes responsive or resonant to a current of somewhat higher frequency, say, 20 Hz.

In this manner, raising the frequencies of stimulating current step by step in an ascending order will also raise the resonant frequency of a sclerotic cell, and repeating this therapy will finally lead to the complete recovery of the elasticity inherent to the membrane of the cell. Then, the various ionic channels will become possible to open again, and normal cell activities will become possible which will lead to the healing of the disease.

The stimulation applied to the cell is null in terms of mean voltage, and through the stimulation calcium is only mechanically removed but does not exist as free ions electrochemically. Accordingly, calcium required by the cell for its vital activity is not lost through the stimulation.

Furthermore, application of a current with specific frequencies does not give any harmful effects on the various cells of human body and their DNA, or rather it is thought beneficial because it may contribute to destruction of viruses and bacteria invading the human body.

To put it more in detail, viruses and bacteria are surrounded by cluster goblets (colloidal membranes) while tissue cells and blood cells of the human body are devoid of such cluster goblets. Thus, application of a current having the frequencies specifically destructive to such cluster goblets may destroy viruses and bacteria selectively without inflicting any damage to the host cells. Or, viruses and bacteria whose cluster goblets have been destroyed after exposure to the current having the frequencies specifically destructive to them will lose a capability to regenerate or migrate, so that they can not develop a resistance to drugs even if they escape destruction brought about by the electric stimulation.

Moreover, stimulation with an electric current having frequencies of 660, 740, 890, 1840, 1998, 5000 and 10000 Hz relaxes human body and gives a good sensation, promotes the secretion of a hormone called oxytocin, increases alpha-wave components in EEG, relieves pain associated with disease, and excites human vigor and rejuvenates the activity of cells.

The lowest frequency used consists of 20 Hz or 666 Hz in most cases. When 20 Hz is used as the lowest frequency, most stimulation may contain 666 Hz in its process to reach the highest frequency. In addition, in most stimulation cases, 20 Hz is followed by 60 Hz and 666 Hz by 727 Hz.

The present inventor found that it is greatly beneficial to have the patient take an aqueous solution of baking soda (sodium bicarbonate) before he/she receives the therapy with the low-frequency therapeutic apparatus of this invention. This is probably because calcium removed from cell membranes during therapy binds to the carbonate group of sodium bicarbonate, to form calcium carbonate which is then excreted.

For therapy, application of at least five sessions continuously with 72 hours intervals on average inserted between adjacent sessions is effective, and for the treatment of the patient seriously ill or weakened by a chronic disease, it is preferable to employ as the initial therapy a session consisting of frequencies not exceeding 1000 Hz.

The frequencies to be used for the therapy with the low-frequency therapeutic apparatus are in the range of 1–10000 Hz, and the reason is as follows.

Firstly, with the conventional low-frequency therapeutic apparatus, for stimulation of degenerate nerves and muscles, passage of electric currents at a rate, for example, of once a few seconds is required, and the wave form of the electric current must have a long duration. This type of apparatus is not for stimulating individual muscle cells, but for stimulating a mass of cells representing a muscle. For stimulating individual muscle cells, it is thought necessary to resort to frequencies not less than 1 Hz.

Setting the upper limit of frequency at 10000 Hz or less was derived from the fact that frequencies exceeding that limit are problematic from the viewpoint of safety to human body, and that a current having 100000 Hz frequency greatly relaxes human body as described earlier.

According to our experiments, it was found that, when a session consists of delivering a series of frequencies step by step in an ascending order and the highest frequency is 5000 or 10000 Hz, repetition of two sessions far enhances the therapeutic effect than otherwise possible.

Repetition of sessions are also effective for enhancing the therapeutic effect as seen, for example, in the treatment of arterial aneurysm. Thus, in this case, repetition of the lowest frequency or 20 Hz twice and the highest frequency or 5000 Hz twice enhances the therapeutic effect as well.

Next, the therapeutic system dependent on the use of the low-frequency therapeutic apparatus described above will be given below with reference to FIG. 7.

This low-frequency therapeutic system comprises an external control unit 34 in place of the frequency control device 18 of the low-frequency apparatus 10 of FIG. 1, or, for example, a computer implemented apart from the oscillating unit 38, so that the external control unit 34 can control the frequency and timing of oscillatory waves through telecommunication lines 36.

The external control unit 34 is composed of a computer, and comprises a memory section 34A, a selection signal delivering section 34B and a hand-manipulated input feeding section 34C.

Further, an oscillating unit 38 incorporates a high-frequency oscillator 38A and a frequency modifier 38B, and receives control signals through an I/O interface 40B from telecommunication lines.

The external control unit 34 and the telecommunication line 36 are also connected to the oscillating unit via the I/O interface 40A.

The actual usage of this low-frequency therapeutic system proceeds as follows.

Firstly, the user (patient or operator) contacts the operator (physician or his/her assistant) of the external control unit 34 through a telecommunication line, informs the operator of the name of his/her disease, and asks for application of the low-frequency therapy.

The operator teaches, according to the name of disease, the manner how the user should apply the therapeutic and inactive electrodes 14 and 16 upon his body, and then feeds the code number representing the name of disease, for example, No. 001 for arteriosclerosis as mentioned earlier through the hand-manipulated input feeding section 34C.

The oscillating unit 38 on the side of the user has been booted up by the external control unit 34 through the telecommunication line 36, and, on receiving an input from the hand-manipulated input feeding section 34C, reads successively frequencies appropriate for the disease from the memory section 34C, and controls the oscillating unit 38 on the side of the user by delivering signals from the selection signal delivering section 34B.

In this way, the frequencies specified for the disease are picked up one after another at specified intervals, and they are delivered across the therapeutic and inactive electrodes 14 and 16.

On completion of the specified treatment period, the external control unit 34 arrests the oscillating unit 38 through the telecommunication line 36.

The therapeutic system as described above is advantageous in that it obviates the need for updating the data concerning individual diseases stored in the memory section of the user's low-frequency therapeutic apparatus even when a new modification is needed or added, or a set of frequencies are introduced for a newly found disease.

Further, when the patient or his/her attendant asks a question or gives information, the physician or expert operator can take a proper action, and thereby prevent the patient or the attendant from being indulged in irrational use of the therapeutic apparatus based solely on his/her dogmatism.

Figure 7:
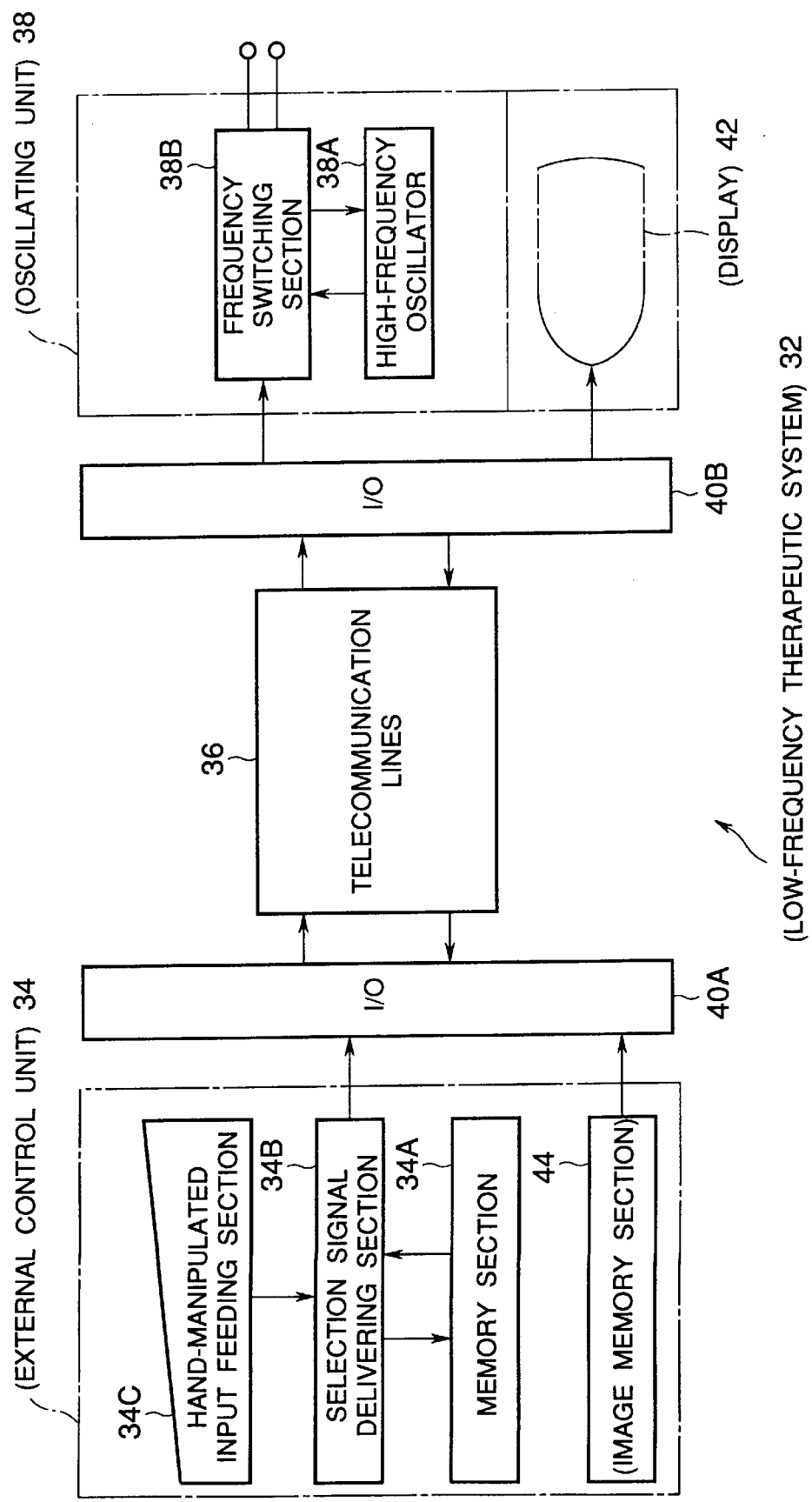
FIG. 7 is a block diagram to illustrate a low-frequency therapeutic system embodying this invention.

As shown by the two-dot-one-dash lines of FIG. 7, monitoring of how the therapeutic and inactive electrodes 14 and 16 are attached on the patient's body may be achieved by introducing, in addition to the oscillating unit 38, a display 42: image data representing the electrode sites corresponding with the disease of interest is read from an image memory section 44 of external control unit 34, and the image is presented on the display 42 for monitoring.

Industrial Applicability

According to this invention, it is possible to bring about an excellent therapeutic effect by relaxing sclerotic cells so as to recover their normal vigor safely without inflicting any adverse effects to the human body, or by annihilating bacteria and viruses or foreign organisms parasitic to human body, and further by enhancing the bodily immunity.

What is claimed is:

1. A method for low-frequency therapy treating diseases by passing a low-frequency electric current from the skin through the body of a patient wherein therapy comprises:
   having the patient ingest a bicarbonate;
   delivering a low-frequency current from at least a part of 1–10000 Hz to the patient step by step in an ascending order at specified time intervals.

2. A method for low-frequency therapy according to claim 1 wherein therapy comprises choosing in advance plural frequencies, and delivering a low-frequency current with those chosen frequencies.

3. A method for low-frequency therapy according to claim 2 wherein the plural frequencies comprise a part chosen from 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

4. A method for low-frequency therapy treating diseases by passing a low-frequency electric current from the skin through the human body wherein therapy comprises choosing the frequencies of low-frequency current from at least a part of 1–10000 Hz, and delivering them step by step in an ascending order at specified time intervals wherein a basic therapy comprising delivering a current with frequencies of 20, 60, 70, 72, 75, 125, 666, 727, 740, 787, 790 and 10000 Hz is initially given in this order, and another therapy comprising delivering a current with frequencies chosen appropriately according to the kind of disease of interest is then given.

5. A method for low-frequency therapy according to claim 2, 3 or 4 wherein therapy comprises passing repetitively plural times through the human body a part of the chosen frequencies of current.

6. A method for low frequency therapy according to any one of claims 2 to 4 wherein therapy comprises passing repetitively through the human body a low-frequency current with the highest frequency of all the chosen frequencies.

7. A method for low-frequency therapy according to any one of claims 2 to 4 wherein the highest of all the chosen frequencies is 10000 Hz.

8. A method for low-frequency therapy treating diseases by passing a low-frequency electric current from the skin through the human body wherein therapy comprises choosing the frequencies of low-frequency current from at least a part of 1–10000 Hz, and delivering them step by step in an ascending order at specified time intervals wherein the lowest of all the chosen frequencies is 20 Hz.

9. A method for low-frequency therapy treating diseases by passing a low-frequency electric current from the skin through the human body wherein therapy comprises choosing the frequencies of low-frequency current from at least a part of 1–10000 Hz, and delivering them step by step in an ascending order at specified time intervals wherein the lowest of all the chosen frequency is 666 Hz.

10. A method for low-frequency therapy treating diseases by passing a low-frequency electric current from the skin through the human body wherein therapy comprises choosing the frequencies of low-frequency current from at least a part of 1–10000 Hz, and delivering them step by step in an ascending order at specified time intervals wherein the highest of all the chosen frequencies is 5000 Hz.

11. A low-frequency therapeutic apparatus (10) comprising a therapeutic electrode (14) to be applied onto a site to be treated, an inactive electrode (16) to be applied on the human body (P) to couple with the therapeutic electrode (14) so that an electric current can be passed through the human body, and an oscillating unit (12) to generate a weak current with a low frequency to be applied across those electrodes (14 and 16), wherein:

the oscillating unit (12) contains a frequency control device (18) which chooses frequencies to be generated from among the plural frequencies chosen in advance from at least a part of 1 to 10000 Hz, and switches those frequencies from the lowest one after another in an ascending order at specified time intervals.

12. A low-frequency therapeutic apparatus (10) according to claim 11 wherein the frequency control device (18) comprises a memory section (22) which stores the data of the plural frequencies chosen in advance according to the kinds of diseases, and a selection signal delivering section (24) which, in response to an instruction signal fed according to the kind of disease of interest, reads the corresponding data of the plural frequencies from the memory section (22), and delivers selection signals thereby to change the frequencies of a wave generated by the oscillating unit (12) in an orderly fashion.

13. A low-frequency therapeutic apparatus (10) according to claim 11 or 12 wherein the plural frequencies comprise a part out of 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

14. A low-frequency therapeutic apparatus comprising a therapeutic electrode to be applied onto a site to be treated, an inactive electrode to be applied on a human body to couple with the therapeutic electrode so that an electric current can be passed through the human body, and an oscillating unit to generate a weak current with a low frequency to be applied across those electrodes wherein the oscillating unit contains a frequency control device which chooses frequencies to be generated from among the plural frequencies chosen in advance from at least a part of 1 to 1000 Hz, and switches those frequencies from the lowest one after another in an ascending order at specified time intervals wherein the basic therapy introduced prior to the therapy specific for the disease of interest comprises delivering a current with frequencies of 20, 60, 70, 72, 75, 125, 666, 727, 740, 787, 790 and 10000 Hz.

15. A low-frequency therapeutic system (32) comprising a therapeutic electrode (14) to be applied onto a site to be treated, an inactive electrode (16) to be applied on the human body (P) to couple with the therapeutic electrode (14) so that an electric current can be passed through the human body, an oscillating unit (38) to generate a weak current with a low frequency ranging from 1 to 10000 Hz to be applied across those electrodes (14 and 16), a frequency selection unit (38B) to change the frequency of a wave generated by the oscillating unit (38) into the frequency designated by an incoming frequency selection signal, and a frequency selection control unit (34) which chooses the data of plural frequencies from among plural frequencies chosen in advance from a part of 1–10000 Hz, arranges them in an ascending order at specified time intervals, and delivers them as frequency selection signals to the frequency selection unit (38B), the oscillating unit (38) and the frequency selection control unit (34) are separated from each other, and the frequency selection control unit (34) at one site delivers the selection signal to the frequency selection device (38B) at different places through a wired or wireless telecommunication line (36).

16. A low-frequency therapeutic system (32) according to claim 15 wherein the frequency selection control unit (34) comprises a memory section (34A) which stores the data of plural frequencies chosen appropriately according to the kinds of diseases, and a signal delivering section (34B) which, in response to an instruction signal fed according to the kind of disease of interest, reads the corresponding data of the plural frequencies from the memory section (34A), and delivers frequently selection signals representing those plural frequencies from the lowest in an ascending order to be the frequency selection unit (38B).

17. A low-frequency therapeutic system (32) according to claim 15, wherein the plural frequencies comprise a part out of 1, 2, 4, 8, 12, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 990, 885, 890, 1500, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

18. A low-frequency therapeutic system (32) according to claim 17 wherein the frequencies of an electric current used for the basic therapy preceding the therapy specific for the disease of interest comprise 20, 60, 70, 72, 75, 125, 666, 727, 740, 787, 790 and 10000 Hz.

19. A low-frequency therapeutic system according to claim 15 wherein therapy comprises passing repetitively plural times through the human body a part of the chosen frequencies of current.

20. A low frequency therapeutic system according to claim 15 wherein therapy comprises passing repetitively through the human body a low-frequency current with the highest frequency of all the chosen frequencies.

21. A low-frequency therapeutic system according to claim 15 wherein the lowest of all the chosen frequencies is 20 Hz.

22. A low-frequency therapeutic system according to claim 15 wherein the lowest of all the chosen frequency is 666 Hz.

23. A low-frequency therapeutic system according to claim 15 wherein the highest of all the chosen frequencies is 10000 Hz.

24. A method for low-frequency therapeutic system according to claim 15 wherein the highest of all the chosen frequencies is 5000 Hz.

25. A method for low-frequency therapy treating diseases by passing a low-frequency electric current from the skin through the human body wherein therapy comprises choosing the frequencies of low-frequency current from at least a part of 1–10000 Hz, and delivering them step by step in an ascending order at specified time intervals and placing portions of the human body into a liquid.

26. A method for low-frequency therapy as claimed in claim 25 wherein said liquid is comprised of water and salt.

* * * * *